(12) United States Patent
Travis et al.

(10) Patent No.: US 7,670,763 B2
(45) Date of Patent: *Mar. 2, 2010

(54) METHOD OF DETERMINING SPERM CAPACITATION

(75) Inventors: Alexander J. Travis, Ithaca, NY (US); Gregory S. Kopf, Leawood, KS (US)

(73) Assignees: Cornell Research Foundation, Inc., Ithaca, NY (US); Trustees of the University of Pennsylvania, Philadelphia, PA (US)

( * ) Notice: Subject to any disclaimer, the term of this patent is extended or adjusted under 35 U.S.C. 154(b) by 567 days.

This patent is subject to a terminal disclaimer.

(21) Appl. No.: 11/591,061

(22) Filed: Nov. 1, 2006

(65) Prior Publication Data

US 2007/0105188 A1 May 10, 2007

Related U.S. Application Data

(62) Division of application No. 10/898,041, filed on Jul. 23, 2004, now Pat. No. 7,160,676.

(60) Provisional application No. 60/489,443, filed on Jul. 23, 2003.

(51) Int. Cl.
*A01N 1/02* (2006.01)
(52) U.S. Cl. .......................... 435/2; 435/325; 530/827; 530/852
(58) Field of Classification Search .................. None
See application file for complete search history.

(56) References Cited

U.S. PATENT DOCUMENTS

| | | | |
|---|---|---|---|
| 6,627,655 B2 | 9/2003 | D'Cruz et al. | |
| 6,835,717 B2 | 12/2004 | Hildreth | |
| 2002/0064849 A1 | 5/2002 | Herr et al. | |
| 2004/0038424 A1 | 2/2004 | Maples | |

FOREIGN PATENT DOCUMENTS

WO        WO 03/100025 A2    12/2003

OTHER PUBLICATIONS

"Bouin's Fixative" 1998 http://www.msu.edu/user/eisthen/lab/methods/anatomy/recipes/bouin.html accessed Apr. 26, 2005.
Cross, *Reorganization of Lipid Rafts During Capacitation of Human Sperm*[1], Biology of Reproduction 71, pp. 1367-1373, (Oct. 2004).
Cross, *Role of Cholesterol in Sperm Capacitation*[1], Biology of Reproduction 59, 1998, pp. 7-11.
Cross, *Effect of Methyl-β-Cyclodextrin on the Acrosomal Responsiveness of Human Sperm*, Molecular Reproduction and Development, 1999, vol. 53, pp. 92-98.
Ensrud et al., *Molecular Biology of the Cell*, Dec. 2000, vol. 11, Supplemental, p. 520a.
Roberts et al., *Inhibition of Capacitation-Associated Tyrosine Phosphorylation Signaling in Rat Sperm by Epididymal Protein Crisp-1*[1], Biology of Reproduction 69, pp. 572-581, (Aug. 2003).
Shadan et al., *Cholesterol Efflux Alters Lipid Raft Stability and Distribution During Capacitation of Boar Spermatozoa*[1], Biology of Reproduction 71, pp. 253-265, (Jul. 2004).
Travis et al., *Expression and Localization of Caveolin-1, and the Presence of Membrane Rafts, in Mouse and Guinea Pig Spermatozoa*, Developmental Biology 240, 2001, pp. 599-610.
Travis et al., *Functional Relationships between Capacitation-dependent Cell Signaling and Compartmentalized Metabolic Pathways in Murine Spermatozoa*, The Journal of Biological Chemistry, 2001, vol. 276, No. 10, Issue of Mar. 9, 2001, pp. 7630-7636.

*Primary Examiner*—Allison M Ford
(74) *Attorney, Agent, or Firm*—Hodgson Russ LLP

(57) ABSTRACT

This invention describes unique patterns of distribution of ganglioside $G_{M1}$ in non-capacitated sperm and demonstrates that the pattern of distribution of $G_{M1}$ undergoes changes that can be correlated with the process of capacitation and/or with acrosomal exocytosis. Accordingly, the present invention discloses a method for determining the ability of sperm to respond to capacitation and/or acrosomal exocytosis stimuli. The method comprises determination of distribution pattern for $G_{M1}$. The method can be used for both diagnostic and predictive purposes when assessing male reproductive fitness, and can also be used to assess the effects on sperm of cryoprotective agents and protocols, and contraceptive agents.

13 Claims, 8 Drawing Sheets

METHOD OF DETERMINING SPERM CAPACITATION

This application is a divisional application of U.S. non-provisional application Ser. No. 10/898,041, filed on Jul. 23, 2004, now U.S. Pat. No. 7,160,676, which in turn claims priority to U.S. provisional application No. 60/489,443, filed on Jul. 23, 2003, the disclosures of which are incorporated herein by reference.

This work was supported by grant numbers KO1-RR00188, PO1-HD-06274 and RO1-HD-045664 from the National Institutes of Health. The government has certain rights in the invention.

FIELD OF THE INVENTION

This invention relates generally to the field of male fertility and more specifically provides a method for determining sperm quality, particularly with regard to assessing the ability of sperm to undergo capacitation by following the pattern of distribution of $G_{M1}$ ganglioside.

DESCRIPTION OF RELATED ART

Ejaculated sperm are not immediately able to fertilize an egg. Rather, they must undergo a process of functional maturation known as "capacitation" (Austin, 1952, Nature, U.S.A., 170:326; Chang, 1951, Nature, U.S.A., 168:697-698). "Capacitation" is generally regarded to be a process that results in the acquisition of hyperactivated motility, and the acquisition of the ability to undergo acrosomal exocytosis. Capacitation results in two specific changes in sperm function. First, the sperm head acquires the ability to undergo acrosomal exocytosis in response to physiological ligands such as zona pellucida proteins or progesterone. Second, the flagellum of the sperm acquires a "hyperactivated" pattern of motility. Although some stimuli for capacitation are species specific, several stimuli for capacitation are common between species. These include the presence of bicarbonate and calcium ions, and the presence of reagents that can act as sterol acceptors thereby mediating the efflux (removal) of sterols from the sperm plasma membrane (e.g. serum albumin, cyclodextrin, high density lipoproteins (HDL), etc.). Currently there are no sensitive and simple markers for capacitation that can be used in a clinical setting. For example, the appearance of protein tyrosine phosphorylation events during the process of capacitation has been described in many species. However, visualization of these events using polyacrylamide gel electrophoresis and immunoblotting can take upwards of 48 hours to perform, making it ill-suited for clinical purposes.

Although it has long been known that mammalian spermatozoa possess different regions in their plasma membranes, information about these domains is largely descriptive. For example, the plasma membrane overlying the acrosome is known to be enriched in sterols. Functionally, it is known that sperm cannot fertilize an egg until sterols have been removed from the sperm plasma membrane by extracellular acceptors in the process of capacitation. However, it is unclear how other lipids are organized in the sperm plasma membrane and if the organization of these lipids might reflect changes associated with the process of capacitation. Accordingly, to address various issues related to male fertility, there is a need to understand lipid patterns during capacitation.

SUMMARY OF THE INVENTION

In the present invention, we demonstrate that mammalian sperm possess lipid rafts enriched in sterols and the ganglioside $G_{M1}$. These may both organize and regulate signaling pathways in somatic cells. These lipids are segregated from other regions of the plasma membrane having a higher content of phospholipids In addition, we present evidence that identifiable and reproducible differences in the pattern of distribution of $G_{M1}$ in these rafts can be correlated with the presence of specific stimuli known to be involved in triggering of the process of capacitation and/or acrosomal exocytosis (the "acrosome reaction").

Further, it was also observed that the pattern of $G_{M1}$ distribution observed was dependent upon the fixation conditions used. Thus, amongst the fixation conditions studied, it was observed that using 4% paraformaldehyde with 0.1% glutaraldehyde and 1 mM $CaCl_2$ resulted in a reproducible pattern of $G_{M1}$ distribution that was closest to the distribution pattern seen in living sperm regardless of whether the sperm were incubated under capacitating or non-capacitating conditions. The use of 0.004% paraformaldehyde as a fixative produces different but reproducible patterns of $G_{M1}$ distribution for sperm incubated under capacitating and/or acrosomal exocytosis inducing conditions. For example, we have observed that in living mouse sperm prior to capacitation, $G_{M1}$ is localized within the sperm head to the plasma membrane overlying the acrosome. $G_{M1}$ has also been observed in the mid-piece and principal piece of the flagellum. After incubating sperm with reagents (singly or in combination) that stimulate capacitation and/or acrosomal exocytosis, a reproducible and stimulus-specific change in the pattern of distribution of $G_{M1}$ was observed. For example, after incubation of sperm with stimuli for capacitation and acrosomal exocytosis, in both living sperm and sperm fixed with 4% paraformaldehyde, 0.1% glutaraldehyde and 1 mM $CaCl_2$, $G_{M1}$ staining in the area of the apical acrosome was seen. Other patterns of $G_{M1}$ staining were seen under other fixation conditions. For example, in sperm fixed with 0.004% paraformaldehyde, $G_{M1}$ staining was seen in the post-acrosomal plasma membrane. In sperm exposed to bicarbonate, staining was observed in the apical acrosome and post-acrosomal region. In sperm exposed to reagents mediating sterol efflux (such as 2-hydroxypropyl)-β-cyclodextrin) a signal in the plasma membrane overlying the acrosome as well as in the post-acrosomal region was observed. In sperm incubated with bicarbonate and mediators of sterol efflux (2-hydroxypropyl)-β-cyclodextrin) and then reagents which induce acrosomal exocytosis (e.g. progesterone), a signal over the apical acrosome alone was observed.

A distinct pattern of $G_{M1}$ distribution was also seen in all other species examined namely, boar, stallion, human, and dog. These sperm have distinct patterns of localization and redistribution of $G_{M1}$ with the redistribution patterns correlating with specific stimuli for capacitation and acrosomal exocytosis. The pattern observed is also dependent upon the fixative used. Based on the observations that $G_{M1}$ is found in the plasma membrane, that it displays a highly reproducible pattern of localization and that it redistributes upon incubation under specific conditions (such as after exposure to capacitating stimuli), several applications are described herein.

In one embodiment a pattern of normal distribution of $G_{M1}$ can be determined in non-capacitated sperm under living or defined fixation conditions. While various fixation conditions can be used for determination of $G_{M1}$ distribution patterns, in a preferred embodiment, fixation conditions are identified which show a distinct and reproducible staining pattern. The distribution pattern of $G_{M1}$ in non-capacitated sperm is designated to be the normal (or control) pattern.

The change in the distribution pattern of $G_{M1}$ in response to capacitating stimuli and/or stimuli inducing acrosomal exocytosis is termed herein as "redistribution". This is distinct from a change in the $G_{M1}$ pattern observed when sperms are fixed with different fixatives. This latter phenomenon is termed as "fixative induced movements" of $G_{M1}$. In one embodiment of the invention, a change in the distribution pattern of $G_{M1}$ (redistribution) in response to stimuli inducing capacitation and/or acrosomal exocytosis under different fixation conditions can be documented. This establishes control patterns for $G_{M1}$ redistribution in response to these stimuli or fixation conditions. These redistribution patterns can be used as controls for assessing factors affecting capacitation.

In another embodiment, the pattern of $G_{M1}$ distribution in non-capacitated sperm and its ability to undergo redistribution in response to specific stimuli for capacitation when compared with a normal population is used as a diagnostic tool for male infertility.

In another embodiment, the pattern of $G_{M1}$ distribution in capacitated sperm and its ability to undergo redistribution associated with acrosomal exocytosis when compared with a normal population is used as a diagnostic tool for male infertility. The information obtained from the capacitation and/or acrosomal exocytosis abilities of sperm in a test sample can be useful for clinicians to identify suitable approaches in assisted reproduction methods.

In another embodiment, the pattern of $G_{M1}$ distribution in non-capacitated sperm in a test sample from an individual and the redistribution of the $G_{M1}$ pattern associated with capacitation and acrosomal exocytosis when compared with a normal sperm sample is used as a predictive tool for evaluating future breeding soundness of the individual.

In another embodiment, the pattern of $G_{M1}$ localization and/or its redistribution associated with capacitation and/or acrosomal exocytosis is used as a marker to evaluate the effect on sperm of potential semen extenders and cryopreservation agents/protocols.

In another embodiment, the pattern of $G_{M1}$ localization and/or its redistribution associated with capacitation and/or acrosomal exocytosis is used as a marker to evaluate potential male contraceptives.

DETAILED DESCRIPTION OF THE INVENTION

Figure 1:
FIG. 1 is a representation of the localization of $G_{M1}$ in the head of a living, motile, murine spermatozoon. The $G_{M1}$ is seen localized to the plasma membrane overlying the acrosome, and is specifically excluded from the post-acrosomal plasma membrane.

The term "$G_{M1}$ staining" or "staining of $G_{M1}$" or related terms as used herein means the staining seen is cells due to the binding of labeled affinity molecules to $G_{M1}$. For example, when fluorescent tagged Cholera toxin b subunit is used for localization of $G_{M1}$, the signal or staining is from the Cholera toxin b subunit but is indicative of the location of $G_{M1}$. The terms "signal" and "staining" are used interchangeably.

The term "capacitated" sperm refers to sperm which have been incubated under conditions which promote the process of capacitation. Specifically, as is known in the art, this requires the presence of bicarbonate and calcium ions in the medium, and the presence of a sterol acceptor such as serum albumin or a cyclodextrin. Capacitated sperm have acquired the ability to undergo acrosomal exocytosis and have acquired a hyperactivated pattern of motility. Consequently, the term "non-capacitated" sperm refers to sperm which are incubated in the absence of the above listed stimuli for capacitation. Such sperm cannot undergo acrosomal exocytosis induced by a physiological ligand such as the zona pellucida, solubilized proteins from the zona pellucida, or progesterone. In addition, sperm incubated under non-capacitating conditions also will not demonstrate hyperactivated motility.

The present invention provides a method for assessing the ability of spermatozoa to undergo capacitation and to evaluate the process of capacitation. The method is based on the novel observation that a unique pattern of distribution of the ganglioside $G_{M1}$ is seen in both living and fixed, non-capacitated sperm, and that this pattern changes in a reproducible manner when the sperm are incubated with different external stimuli mimicking the events during capacitation and/or acrosomal exocytosis. Since changes in the pattern of distribution of $G_{M1}$ were found to be dependent upon the fixation conditions, based on the teachings and examples provided herein, fixation conditions providing the most distinction between non-capacitated sperm and capacitated sperm with or without acrosomal exocytosis can be determined for different species. Because of different patterns of $G_{M1}$ generated under different fixation conditions, it is preferable to run control samples under same fixation conditions as the test samples. In a more preferred embodiment, the control samples are run in parallel.

Reproducible changes in the pattern of $G_{M1}$ localization can be observed in sperm that are first incubated with different external stimuli, and then are fixed under defined conditions. Manipulating either/both the incubation conditions and the fixation conditions, can therefore give an investigator different types of complementary information. For example, to evaluate if a given population of mouse sperm has normal organization of membrane sub-domains under non-capacitating conditions and/or in response to stimuli for capacitation and exocytosis, one could determine $G_{M1}$ staining in living cells or in cells fixed with 4% paraformaldehyde, 0.1% glutaraldehyde, and 1 mM $CaCl_2$. While not intending to be bound by any particular theory, it is considered that under these fixation conditions, the lipids are locked in place as they are in the living sperm. In another embodiment, to evaluate the percent of sperm that are capable of responding to stimuli for capacitation thereby providing predictive/diagnostic information about the ability of the sperm to undergo specific stages of capacitation and be competent to fertilize an egg, the cells could be fixed with 0.004% paraformaldehyde, prior to labeling to localize $G_{M1}$. Under this fixation condition, we see reproducible patterns of movements of $G_{M1}$ specifically induced in only those cells that are responding to the stimuli. These patterns can be compared to "normal" or "control" patterns of $G_{M1}$ distribution in sperm from fertile males incubated and fixed under the same conditions. Comparison of the sperm in the test sample with the normal sperm would then be the basis of declaring the sperm normal or abnormal.

For visualization of $G_{M1}$ in living sperm, the spermatozoa are typically washed with a standard base medium (e.g. Modified Whitten's medium, or other media which support the function of sperm of different species) and incubated with an affinity molecule for $G_{M1}$ which has a detectable moiety on it. Since $G_{M1}$ has extracellular sugar residues which can serve as an epitope, it can be visualized without having to fix and permeabilize the cells. However, fixation of the cells will result in better preservation of the specimen, easy visualization (compared to discerning patterns in swimming sperm) and allow longer visualization time. Based on the teachings provided herein, determination of fixation conditions that will produce a reproducible pattern of distribution of $G_{M1}$ can be done by those skilled in the art. Various fixatives known for histological study of spermatozoa are within the purview of those skilled in the art. Suitable fixatives include paraformaldehyde, glutaraldehyde, Bouin's fixative, and fixatives comprising sodium cacodylate, calcium chloride, picric acid, tannic acid and like. In a preferred embodiment, paraformaldehy, glutaraldehyde or combinations thereof are used.

In the mouse, when using 0.004% paraformaldehyde as a fixative (Fixative A in Table 1), almost all non-capacitated sperm show a post-acrosomal pattern. After incubation of sperm with bicarbonate alone, approximately 40% of the cells show signal over the apical acrosome as well as over the post-acrosomal plasma membrane. After incubation of the sperm with cyclodextrin, approximately 40% of the cells showed a diffuse pattern throughout the head of the sperm. Note: in the table, Pattern A stands for "acrosomal," pattern "D" stands for diffuse, pattern "AA/PA" stands for "apical acrosome and post-acrosomal" and "PA" stands for "post-acrosomal." "NC" stands for non-capacitating and "CAP" stands for capacitating (in the presence of both cyclodextrin and bicarbonate).

When using 1.25% paraformaldehyde, 2.5% glutaraldehyde, 100 mM sodium cacodylate and 0.5 mM $CaCl_2$ as a fixative (Fixative B in Table 1), approximately 80% of the sperm incubated under non-capacitating conditions showed signal over the acrosomal plasma membrane, with the remainder having a diffuse pattern. When incubated in the presence of a sterol acceptor, approximately 60% of the sperm exhibit a diffuse pattern.

When using 4% paraformaldehyde, 0.1% glutaraldehyde and 1 mM $CaCl_2$ as a fixative (Fixative C in Table 1), approximately 80% of the sperm incubated under any of the conditions display signal over the acrosomal plasma membrane. The remainder display a diffuse pattern.

TABLE 1

| | | Pattern | | | |
|---|---|---|---|---|---|
| Fixative | Incubation Condition | A | D | AA/PA | PA |
| A | NC | ns* | 7.3 | 17.3 | 72.8 |
| | NaHCO$_3$ | Ns | 3.2 | 34.9 | 61.8 |
| | 2-OHCD | Ns | 40.4 | 28.8 | 37.9 |
| | CAP | Ns | 33.6 | 26.9 | 39.6 |
| B | NC | 75.2 | 0 | 0 | 24.8 |
| | NaHCO$_3$ | 49.0 | 0 | 0 | 51.0 |
| | 2-OHCD | 41.8 | 0 | 0 | 58.2 |
| | CAP | 37.9 | 0 | 0 | 62.3 |
| C | NC | 83.7 | 0 | 0.2 | 16.2 |
| | NaHCO$_3$ | 78.2 | 0 | 0.9 | 20.8 |
| | 2-OHCD | 80.5 | 0 | 0.2 | 19.4 |
| | CAP | 79.6 | 0 | 0 | 20.4 |

In living normal sperm (unfixed), almost all of the cells show pattern A.

During the process of capacitation, sperm are known to respond to external stimuli such as bicarbonate and calcium ions, and mediators of sterol efflux such as 2-hydroxy-propyl cyclodextrin, methyl-β-cyclodextrin, serum albumin, high density lipoprotein, phospholipids vesicles, liposomes etc. An identifiable change in the $G_{M1}$ distribution pattern has been observed when spermatozoa are exposed to these stimuli in vitro.

Unique $G_{M1}$ staining patterns have been observed in mouse, horse, boar, dog and human sperm. In addition, abnormalities in $G_{M1}$ distribution can be seen in the heads of sperm having morphologically-obvious flagellar defects. Thus, localization of $G_{M1}$ can be used to indicate defects in sperm membranes not detectable by normal morphological observations without the $G_{M1}$ staining. For example, flagellar defects (such as both proximal and distal cytoplasmic droplets) may not necessarily indicate abnormal capacitation ability. Visualization of $G_{M1}$ distribution patterns and comparison with controls will provide a more accurate determination of the capacitation ability.

The distribution pattern of $G_{M1}$ in live or fixed sperm can be obtained by using affinity binding techniques. A molecule having specific affinity for the $G_{M1}$ ganglioside can be used. The affinity molecule can be directly linked to a detectable label (such as a fluorophore) or may be detected by a second affinity molecule which has a detectable label on it. For example, the b subunit of cholera toxin is known to specifically bind to $G_{M1}$. Therefore, a labeled (such as fluorescent labeled) cholera toxin b subunit can be used to obtain a pattern of distribution of $G_{M1}$. Alternatively, a labeled antibody to the cholera toxin b subunit can be used to visualize the pattern of $G_{M1}$ staining. The detectable label is such is that it is capable of producing a detectable signal. Such labels include a radionuclide, an enzyme, a fluorescent agent or a chromophore. Staining and visualization of $G_{M1}$ distribution in sperm is carried out by standard techniques. Affinity molecules other than the b subunit of cholera toxin can also be used. These include polyclonal and monoclonal antibodies. Specific antibodies to $G_{M1}$ ganglioside can be generated by routine immunization protocols, or can be purchased commercially (Matreya, Inc., State College, Pa.). The antibodies may be raised against $G_{M1}$ or, since gangliosides in general, are known to be weak antigens, specific antibodies to $G_{M1}$ can be generated by using peptide mimics of relevant epitopes of the $G_{M1}$ molecule. Identification and generation of peptide mimics is well known to those skilled in the art.

$G_{M1}$ in sperm lipid rafts can be visualized on living, motile sperm, or on sperm that are fixed. We demonstrate that when sperm are fixed under different conditions, different patterns of localization can be seen. These patterns reflect whether the sperm have responded to capacitating stimuli in the medium with which they were incubated (for example, bicarbonate or agents mediating sterol efflux, two of the critical upstream stimuli for capacitation). In this way, the invention allows one to track the percentage of sperm in a population, which are capable of responding to capacitating stimuli. In addition, incubation of the sperm under capacitating conditions and then adding a reagent which induces acrosomal exocytosis for example: progesterone, recombinant/solubilized or solid proteins from the zona pellucida (such as the ZP3 protein in mouse or homologs from other species), carbohydrate moieties (such as the carbohydrate moieties on ZP3), calcium ionophore, or other pharmacologic agents (such as lysophosphatidylcholine) allows one to track the percentage of sperm in a population which are capable of responding to that stimulus. Therefore, the invention allows an individual (such as scientist, clinician, or herd health manager) to find out detailed information regarding the ability of sperm to respond to different stimuli for capacitation and acrosomal exocytosis.

Accordingly, in one embodiment, the invention provides a method for determining the pattern of $G_{M1}$ distribution in non-capacitated sperm in a species and determining the change in this pattern (redistribution) during capacitation. A control or standard pattern of $G_{M1}$ staining can be obtained from a sample of normal semen. Typically, a control pattern can be generated for a given species by evaluating the pattern from a large sample (such as about 20-30) of individuals who have been classified as fertile according to acceptable criteria. In the case of humans, such criteria have been established by the World Health Organization (WHO). Further, the American College of Theriogenology publishes guidelines for normal semen parameters for several species. The normal pattern of the redistribution of $G_{M1}$ in response to capacitating stimuli can also be determined for each species. $G_{M1}$ staining can be observed for each sample to be tested in several microscopic fields (typically 100-200 sperm). Various staining patterns are identified and a frequency chart is obtained for each pattern. Staining patterns that are most abundant in the normal samples are designated as normal staining patterns. It is expected that even in the normal samples some deviations from the most abundant staining pattern will be observed. The number and frequency of such deviations can be documented to establish a range of frequencies for each type of deviation in normal semen. This will serve as a control or standard staining pattern for comparison with test samples.

When evaluating a test sample, $G_{M1}$ staining can be carried out as described above and the staining pattern examined. The number and frequency of each type of staining pattern is recorded and the data for each test sample is compared to the control pattern. Samples may be designated as abnormal and suggestive of sub-fertility/infertility because of staining patterns unique to the test samples (i.e., abnormal localization as shown herein in FIGS. 8A and 8B) or on the basis of deviated frequencies of staining patterns from that observed in the controls.

In another application of this invention, the effect of various environments (such as storage media, contraceptives or incubation media etc) or various protocols relating to storage, processing of semen or contraception can be determined by assessing $G_{M1}$ distribution. This will serve as an indicator of the integrity of the sperm plasma membrane, the integrity/organization of plasma membrane sub-domains, and the ability of sperm to undergo capacitation and/or acrosomal exocytosis. For these applications, $G_{M1}$ distribution patterns or localization following the exposure, storage or incubation of sperm in/to various environments or protocols is compared to a control pattern. The control pattern can be an established standard or may be a generated from samples run in parallel with the test sample but without the presence of the particular attribute being tested.

For example, $G_{M1}$ distribution and its redistribution during capacitation is used for evaluation of sperm storage media such as semen extenders and cryopreservation media. In a variety of species (e.g. bovine, equine, porcine, ovine, canine, murine and human), cryopreservation and the use of semen extenders to ship cooled semen, or to wash/dilute fresh or previously frozen sperm, is an important part of assisted reproduction and in the generation of transgenic animals. In addition, the freezing of sperm for long-term storage also requires the use of agents and protocols that minimize damage to these cells. In most cases, the semen extenders and agents used as protectants against damage during freezing and thawing rely on poorly defined media components (e.g. milk or egg yolks). Optimization of such reagents and protocols continues to be of primary commercial importance, and the development of a completely defined protective medium would give tremendous commercial advantage regarding quality control. Because $G_{M1}$ has been found on the plasma membrane of sperm in discrete locations in sperm prior to and during capacitation, and during acrosomal exocytosis, the localization of $G_{M1}$ can be used as a marker for how exposure to such reagents and protocols affects the fragile organization of the membrane sub-domains in these cells. In addition, because $G_{M1}$ redistribution reflects a sperm's response to capacitating stimuli and stimuli for acrosomal exocytosis (both requirements for the sperm to be able to fertilize an egg), the localization of $G_{M1}$ can be used as a marker for how exposure to such reagents and protocols can affect the ability of the sperm to undergo capacitation and acrosomal exocytosis. Moreover, exogenous $G_{M1}$ has been demonstrated to affect the signaling activity of a variety of cell types. We have found that commonly used commercial semen extenders, often contain high amounts of exogenous $G_{M1}$. Such data suggest that the appearance of this ganglioside in media might be having pro- or anti-capacitation effects on the sperm, and might be affecting the distribution of $G_{M1}$ within the sperm.

To be useful in this regard, fresh semen can be collected, washed (typically accomplished by low centrifugation and resuspension in the medium or passing through cheesecloth to remove the gel fraction) and aliquots exposed to a candidate semen extender/cryopreservation media and protocols. Sperm from each group can be labeled with the marker for the $G_{M1}$ at various stages through this process, and either visualized directly with epifluorescence, or incubated under capacitating conditions and then visualized after washing.

Alternatively, sperm from each group could be fixed at various stages through a process of cryopreservation or during incubations with stimuli for capacitation and/or acrosomal exocytosis, and then labeled, washed, and visualized. Comparison against a fresh ejaculate or an already established standard can be carried out to determine if there has been a loss or gain of the ability to respond to capacitation and/or acrosomal exocytosis stimuli.

In another embodiment, $G_{M1}$ distribution and its redistribution during capacitation and acrosomal exocytosis is used for evaluation of male fertility deficiencies. Idiopathic male infertility is an important reproductive concern in a variety of species, including the human. In agricultural and veterinary settings, breeding soundness exams are an important component of evaluating male fertility. However, most assessments short of fertility trials are based on gross observations of sperm motility and morphology, as opposed to functional assays. Because $G_{M1}$ is a marker for the organization of discrete plasma membrane sub-domains, and because its redistribution reflects a response to capacitating stimuli and stimuli for acrosomal exocytosis, the localization of this sub-domain in sperm can provide information regarding both the organization of sperm at the ultra-structural level, and the ability of these cells to undergo changes associated with the acquisition of fertilizing ability. Therefore, an assessment of the localization of $G_{M1}$ would provide detailed information not currently available. In addition, such a test could be performed within hours, as opposed to other tests which require at least two days to perform.

To be used as a diagnostic assay when assessing male fertility, sperm can be collected and washed according to standard protocols well known in the art. They can then be labeled with the reagent specific for $G_{M1}$, or they can be incubated under non-capacitating and capacitating conditions (including stimuli for acrosomal exocytosis, if desired and then labeled. Alternatively, they could be fixed and then labeled, or incubated under non-capacitating and capacitating conditions, fixed and then labeled. The cells can be washed gently with the base medium and then visualized by standard fluorescence microscopy. Because the assay requires little time when compared with other methods of assessing sperm function (e.g. hamster zona penetration tests or western blots to assess protein tyrosine phosphorylation), knowledge gained from this investigation could enable the physician or veterinarian to decide between several methods of assisted reproduction such as intra-cytoplasmic sperm injection (if the sperm were abnormal), or artificial insemination or in vitro fertilization (if the sperm showed normal patterns of $G_{M1}$ prior to and upon exposure to capacitating stimuli and stimuli for acrosomal exocytosis). Obtaining this information for IVF would help to identify problem donors early in the process which can result in cost and time savings. Similarly, identification of problem males in species where breeding is routinely done, can result in significant cost and time savings.

In another embodiment, $G_{M1}$ distribution and its redistribution during capacitation and/or acrosomal exocytosis is used to predict future male reproductive fitness. In agricultural and veterinary settings, breeding soundness exams are an important component of evaluating male fertility. Particularly in cattle, evaluation of the future reproductive success of a given bull has significant economic impact. Initial assessments are based on gross observations of sperm motility and morphology, as opposed to functional assays, and then are typically followed up over a period of months and years with fertility trials. Because $G_{M1}$ is a marker for the organization of discrete plasma membrane sub-domains, and because its redistribution reflects a response to capacitating stimuli and acrosomal exocytosis, the localization of this sub-domain in sperm can provide information regarding both the organization of sperm at the ultra-structural level, and the ability of these cells to undergo changes associated with the acquisition of fertilizing ability. Therefore, an assessment of the localization of $G_{M1}$ would provide detailed information not currently available, potentially allowing herd managers to select for or against the continued use of a given male (bull in the case of cattle). In addition, such a test could be performed within hours, as opposed to other tests which require at least two days to perform.

To be used as a predictive indicator when assessing male fertility, sperm can be collected and washed according to standard protocols. They could be labeled immediately with the reagent specific for $G_{M1}$, or they could be incubated under non-capacitating and capacitating conditions, and/or conditions promoting acrosomal exocytosis, and then labeled. Post-incubation, they can be fixed then labeled, or labeled then fixed, or labeled as live cells, depending on the specific information desired. The cells can be washed gently and then visualized by standard fluorescence microscopy. Because the assay requires little time when compared with other methods of assessing sperm function (e.g. hamster zona penetration tests or western blots to assess protein tyrosine phosphorylation), knowledge gained from this investigation could enable the herd manager or veterinarian to decide whether the individual male had sperm which were normal with respect to the organization of their plasma membrane sub-domains and in their response to capacitating stimuli and/or stimuli for acrosomal exocytosis Because capacitation is essential for a sperm to fertilize an egg, a male having a higher percentage of abnormal sperm than typical for its species could be selected to be removed from consideration for future breeding. This would result in considerable economic savings.

In another embodiment, $G_{M1}$ redistribution in response to capacitating stimuli or stimuli for acrosomal exocytosis can be used for evaluation of potential contraceptives. Localization of $G_{M1}$ in sperm can be used to screen for the efficacy of male contraceptives, as well as a general tool for assessment of environmental toxins on male reproduction. The effect of male contraceptives, including topical spermicides as well as parenteral and enteral pharmacologics, on sperm plasma membranes can be evaluated by using $G_{M1}$ as a marker for the organization of discrete sub-domains known to exist in normal sperm. Because the reagent specific for $G_{M1}$ can be detected by simple fluorescence microscopy, such a test could be performed quickly and conveniently in almost any research setting, or could be performed by a dedicated lab. Assessments of sperm both prior to and after incubation under capacitating conditions could be performed to look for subtle effects on fertilizing ability. Such tests could be performed as described above. To establish a correlation between capacitation and $G_{M1}$ pattern for a given species, capacitation can be established by standard methods such as immunoblotting for protein tyrosine phosphorylation events.

The invention is further described through the examples presented below which are intended to be illustrative and not restrictive in any way.

Example 1

To localize the ganglioside, $G_{M1}$, in living, motile sperm, $5 \times 10^6$ murine sperm were incubated with 10 μg/ml Cholera toxin b subunit with an Alexa-Fluor fluorescent tag ("CTb," Molecular Probes, Eugene, Oreg.) in 750 μl of modified Whitten's medium (22 mM HEPES, 1.2 mM $MgCl_2$, 100 mM NaCl, 4.7 mM KCl, 1 mM pyruvic acid, 4.8 mM lactic acid hemi-calcium salt, pH 7.35). Glucose (5.5 mM), $NaHCO_3$ (10 mM), and (2-hydroxypropyl)-β-cyclodextrin (2-OHCD; 3 mM) were supplemented as needed for 10 minutes at 37° C. in the dark. After washing at 37° C., CTb was seen specifically in the plasma membrane overlying the acrosome (FIG. 1). The fluorescence was detected with a Nikon TE2000 microscope equipped with an OpenLab/Volocity imaging system (Improvision, Lexington, Mass.). The same pattern of fluorescence was seen when sperm were fixed with 4% paraformaldehyde and 0.1% glutaraldehyde.

Example 2

To investigate the existence of lipid rafts in murine sperm, sterols, caveolin-1, and the ganglioside, $G_{M1}$, were localized by fluorescence methods. Caveolin-1 is often used as a marker for lipid rafts in that it requires interaction with a sterol to attach to a membrane, and often fractionates with lipid raft membrane sub-domains. It should be noted that caveolin cannot be detected in living cells by indirect immunofluorescence because the epitopes recognized by the caveolin antibody are intracellular. Similarly, filipin must be visualized in fixed cells as the autofluorescence is weak and easily quenched, hence movement of the cells during a long exposure time would cause a loss of resolution.

Figure 2:
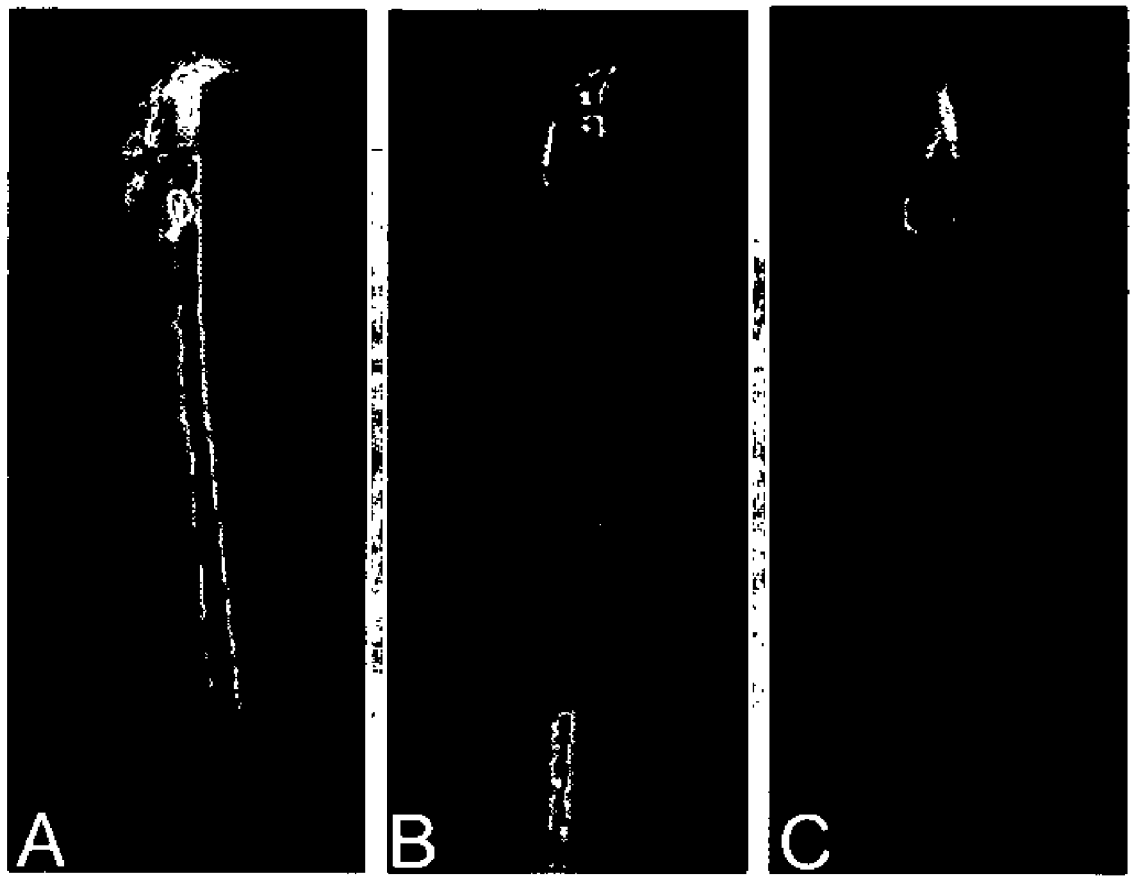
FIGS. 2A-C are representations of the localization of sterols, caveolin, and $G_{M1}$ in fixed murine sperm. Filipin was used to visualize sterols by its inherent auto-fluorescent properties (A). Caveolin-1 was localized via indirect immunofluorescence (B). $G_{M1}$ was localized using a fluorescence-labeled b subunit of cholera toxin (C). This cell, incubated under non-capacitating conditions, was fixed using 0.004% paraformaldehyde, showing localization of $G_{M1}$ to the post-acrosomal plasma membrane under this fixation condition

To localize sterols in murine sperm, we incubated $1 \times 10^6$ sperm with 0.005% filipin (w/v, in dimethyl formamide) (Sigma, St. Louis, Mo.) in 1 ml of modified Whitten's medium (i.e. non-capacitating conditions). Sperm were washed twice by centrifugation and resuspended in medium containing 0.004% paraformaldehyde (w/v). Filipin-sterol complexes (FSC) were visualized in sperm on a heated stage and chamber by the auto-fluorescence properties of filipin. FSC were seen in the acrosomal plasma membrane, the connecting piece, and the flagellum (FIG. 2A), which is consistent with published reports using freeze-fracture electron microscopy. Caveolin-1 was localized using indirect immuno-fluorescence (polyclonal antiserum #C13630, Transduction Laboratories, Lexington, Ky.), on cells permeabilized with methanol and fixed with 2% paraformaldehyde. Caveolin-1 was seen in the acrosomal plasma membrane, midpiece and principal piece (FIG. 2B). Control sperm incubated with the secondary antibody alone were not labeled (data not shown). To localize $G_{M1}$ in fixed sperm, $5 \times 10^6$ murine sperm were incubated with 10 μg/ml CTb in 750 μl of modified Whitten's medium for 10 minutes at 37° C. in the dark. The sperm were fixed with 0.004% paraformaldehyde at 37° C., and then washed gently. Interestingly, CTb fluorescence was seen specifically in the post-acrosomal plasma membrane of the sperm head, the midpiece, the annulus, and a thin line down the length of the principal piece (FIG. 2C).

We have observed that the movement of $G_{M1}$ from the plasma membrane overlying the acrosome to the post-acrosomal plasma membrane can also occur upon cell death, so long as a cross-linking reagent (such as CTb or an anti-ganglioside antibody) is used, and the sperm had not been exposed to capacitating stimuli (see below). Thus, the localization of $G_{M1}$ in sperm depends upon the response of the sperm to molecular stimuli for capacitation, the reagent used to visualize the $G_{M1}$, and the fixation condition used.

Example 3

This example demonstrates the changes in the pattern of $G_{M1}$ distribution (redistribution) that are observed under conditions which are known to induce or which accompany the process of capacitation. In Example 2, it was demonstrated that the plasma membrane overlying the acrosome was enriched in sterols, whereas the post-acrosomal plasma membrane was enriched in $G_{M1}$, when the sperm were incubated under non-capacitating conditions and then fixed in 0.004% paraformaldehyde. This segregation was remarkably consistent in non-capacitated sperm. It has been documented that exposure of sperm to sterol acceptors such as 2-hydroxypropyl cyclodextrin (2-OHCD) or bovine serum albumin (BSA) causes the loss of most FSC from the plasma membrane overlying the acrosome, and allows some FSC to diffuse laterally into the post-acrosomal plasma membrane. This finding is consistent with the loss of sterols causing an increase in membrane fluidity, and promoting lateral diffusion. To investigate the dynamics of the rafts enriched in $G_{M1}$, sperm were incubated as follows: under non-capacitating conditions in a modified Whitten's medium containing $Ca^{++}$; with 10 mM $HCO_3^-$; with 3 mM 2-OHCD; or with both 10 mM $HCO_3^-$ and 3 mM 2-OHCD (capacitating). The last condition has been shown to cause the full pattern of protein tyrosine phosphorylation associated with capacitation, while leaving the sperm functional to perform in vitro fertilization (data not shown). Incubation with $Ca^{++}$, $HCO_3^-$, or 2-OHCD alone is not sufficient to cause either tyrosine phosphorylation or capacitation. Sperm were incubated for 45 minutes under these conditions, then CTb was added for a 10 minute incubation at a final concentration of 10 μg/ml prior to washing. To sperms were then fixed in 0.004% paraformaldehyde. Similar patterns were seen when sperm were incubated under the various conditions, then fixed with 0.004% paraformaldehyde and then labeled with CTb.

Figure 3:
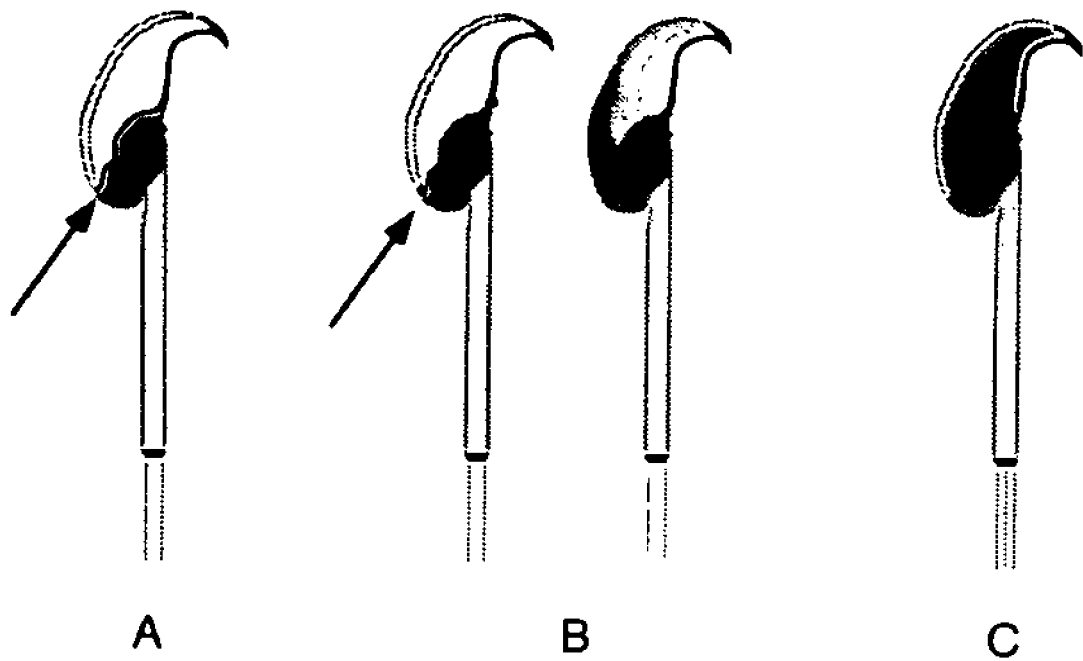
FIGS. 3A-3C are representations of the various patterns of localization of $G_{M1}$, as visualized with Cholera toxin b (CTb), in murine sperm incubated under non-capacitating and capacitating conditions. These patterns are seen when sperms are fixed with 0.004% paraformaldehyde. Two localization patterns are shown grouped together as pattern "B." This is because the increase in intensity of labeling seen at the edges of the sub-acrosomal ring were often seen in the same cells having a shift in CTb labeling along the edge of the apical acrosome (Arrows indicate the sub-acrosomal ring in pattern A and the increase in intensity seen in pattern B.). Pattern "C" was defined on the basis of a similar intensity of fluorescence between the acrosomal and post-acrosomal domains. Schematics at the top of the figure are shown with inverted light intensities.
Figure 3:
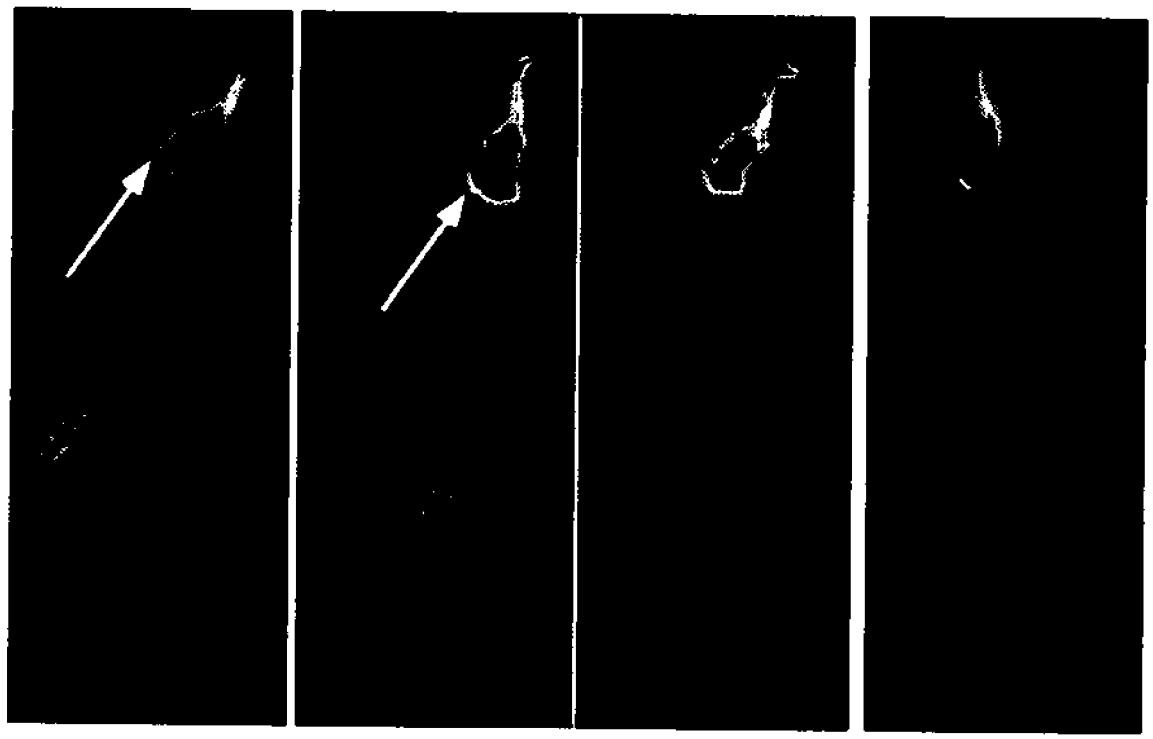
Figure 4:
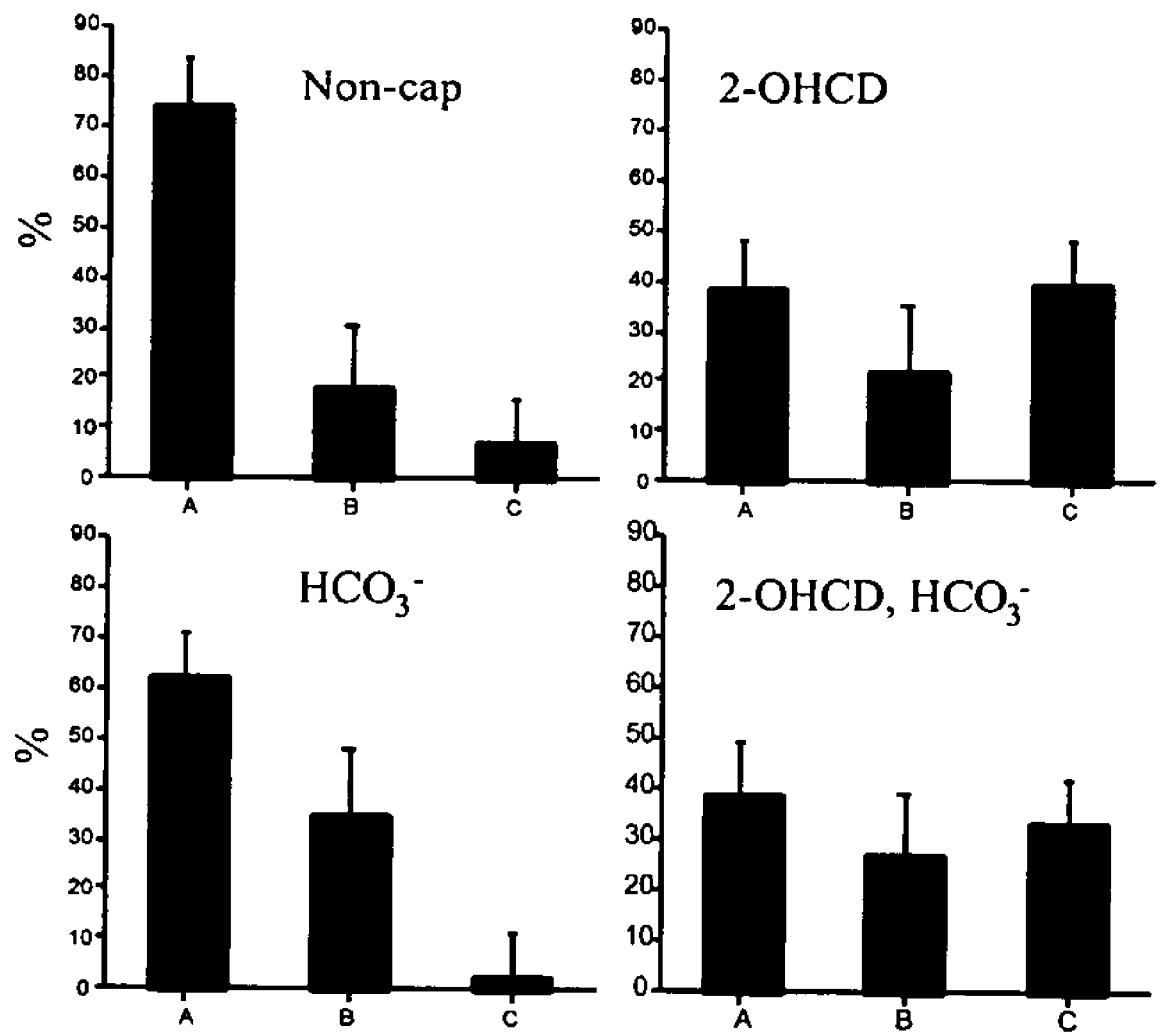
FIG. 4 is a graphical representation of the relative distribution of patterns seen in FIGS. 3A and 3B, when murine sperm are incubated under different conditions. The figure shows the mean percentages of sperm having patterns A, B and C with the associated standard deviations. Between four to eight experiments were performed for each condition, and at least 100 cells were counted per condition per experiment.

FIG. 3A is an example of the most abundant different patterns seen under non-capacitating and capacitating conditions. FIG. 4 shows the relative distribution of these patterns under non-capacitating and capacitating conditions. As can be seen in FIG. 4, the majority of sperm incubated under non-capacitating conditions had a type "A" pattern of labeling with CTb. Incubation with $HCO_3^-$ stimulated a shift from pattern "A" to pattern "B." Incubation with either 2-OHCD alone, or in conjunction with $HCO_3^-$, caused almost identical shifts to pattern "C." None of the treatment conditions caused observable change in the localization patterns over the midpiece, annulus, or principal piece. It should also be noted that 45 minute incubations were chosen to minimize the percent of sperm that underwent spontaneous acrosomal exocytosis. Because $G_{M1}$ localizes specifically to the plasma membrane, and the CTb used has a particularly bright fluorescence, the integrity of the sperm membranes (and state of the acrosome) was clearly visible. Longer incubation times would be expected to show more pronounced shift to pattern C under conditions promoting sterol efflux. The following criteria for counting and assignment of a sperm into one of the patterns were used, including 1) counting only morphologically normal sperm labeled with equal intensity, 2) counting only sperm in areas having a uniform background signal, 3) assigning sperm based on the relative intensities of fluorescence in the acrosomal and post-acrosomal regions, and 4) counting all the sperm in multiple high power fields. The latter point was important to avoid investigators' sub-consciously counting a particular pattern first, and then stopping when a count of 100 cells was reached. To compare the shifts in population tendencies, the numbers were converted to percentages prior to graphing.

Example 4

Figure 5A:
FIGS. 5A and B are representations of the pattern of $G_{M1}$ localization seen in live murine sperm after incubation under capacitating conditions, and exposure to a reagent which induces acrosomal exocytosis (e.g. progesterone). A similar pattern is observed with cells fixed with 4.0% paraformaldehyde, 0.1% glutaraldehyde, and 1 mM $CaCl_2$.
Figure 5B:
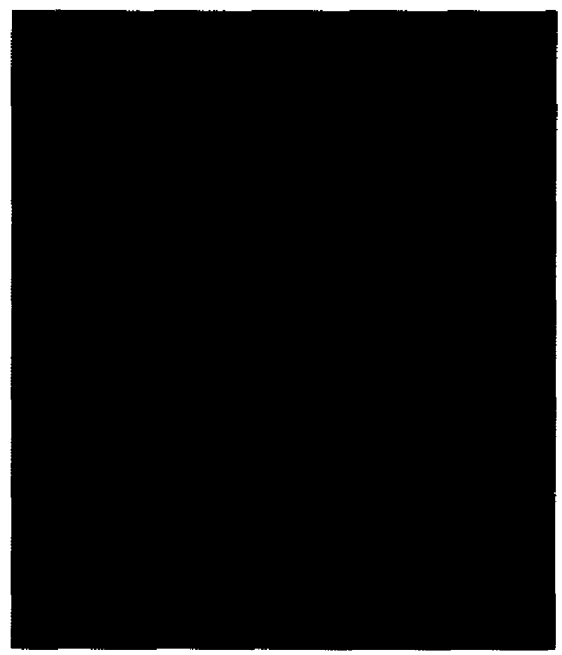
Figure 6A:
FIGS. 6A-6D are representations of several patterns of $G_{M1}$ localization seen in a normal sample of non-capacitated bull sperm.
Figure 6B:
Figure 6C:
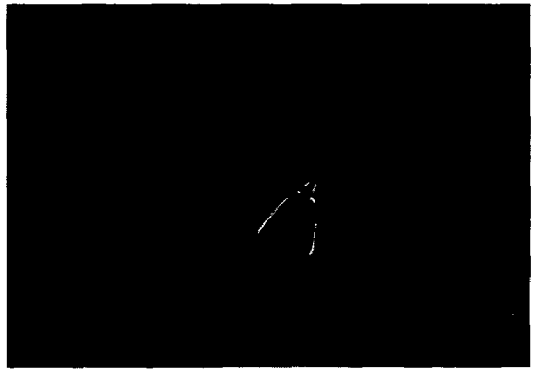
Figure 6D:
Figure 7A:
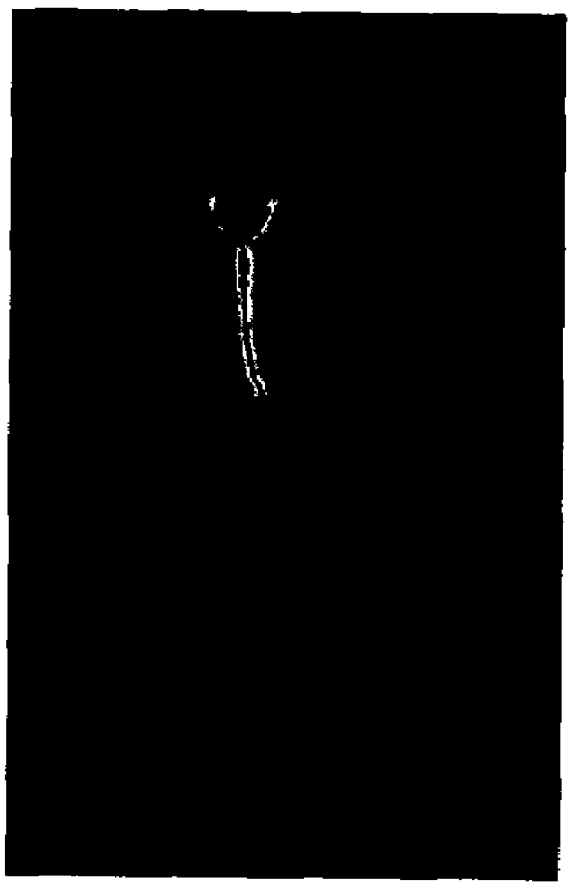
FIGS. 7A and 7B are representations of two patterns of $G_{M1}$ localization seen in a normal sample of non-capacitated dog sperm.
Figure 7B:
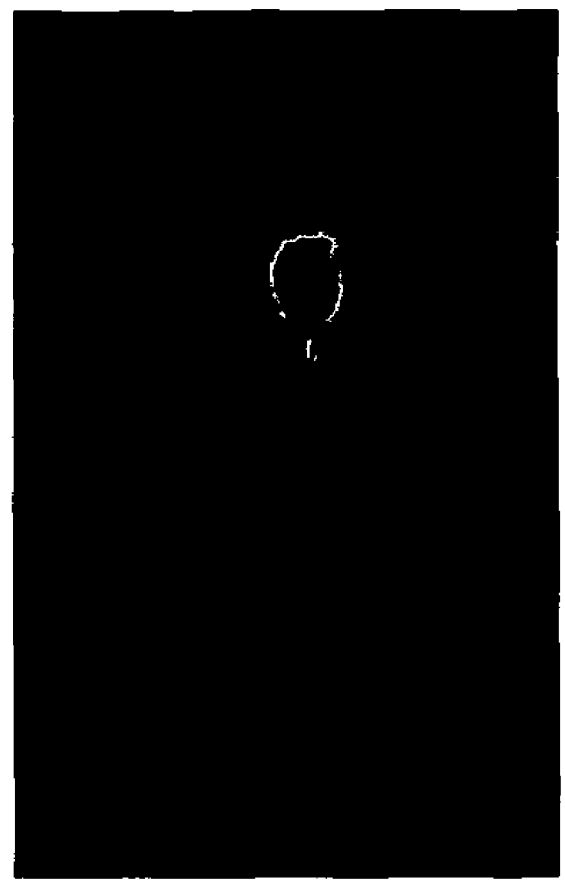

This example demonstrates patterns of $G_{M1}$ localization in murine sperm after incubation under capacitating conditions followed by incubation in the presence of 10 μg/ml progesterone for 10 minutes. $G_{M1}$ labeling was carried out as described above in Example 3. The results are shown in FIGS. 5A and 5B. Labeling of $G_{M1}$ is seen concentrated in the region of the apical acrosome. Both sperm were incubated with progesterone. Both have signal over the apical acrosome, but not over the entire acrosomal plasma membrane. The image on the left shows a linear region of clearing between two brighter lines on the curve of the sperm head. The one on the right shows less of a clearing, with the fluorescence more even over the apical acrosome.

Example 5

This example demonstrates patterns of $G_{M1}$ localization in bull sperm and dog sperm. $G_{M1}$ labeling was carried out as described in Example 2, except using TALP (Tyrode's Albumin/Lactate/Pyruvate) medium for the bovine sperm (Parrish, et al., 1988, Biology of Reproduction, 38:1171-1180), and canine capacitation medium for the dog (Mahi and Yanagimachi, 1978, *Gamete Research*, 1:101-109). The results are shown in FIGS. 6A-6D (bull) and 7A-7B (dog). Several patterns of $G_{M1}$ localization seen in a normal sample are shown. These patterns appear to be similar to patterns seen in the mouse.

Example 6

Figures 8A, 8B:
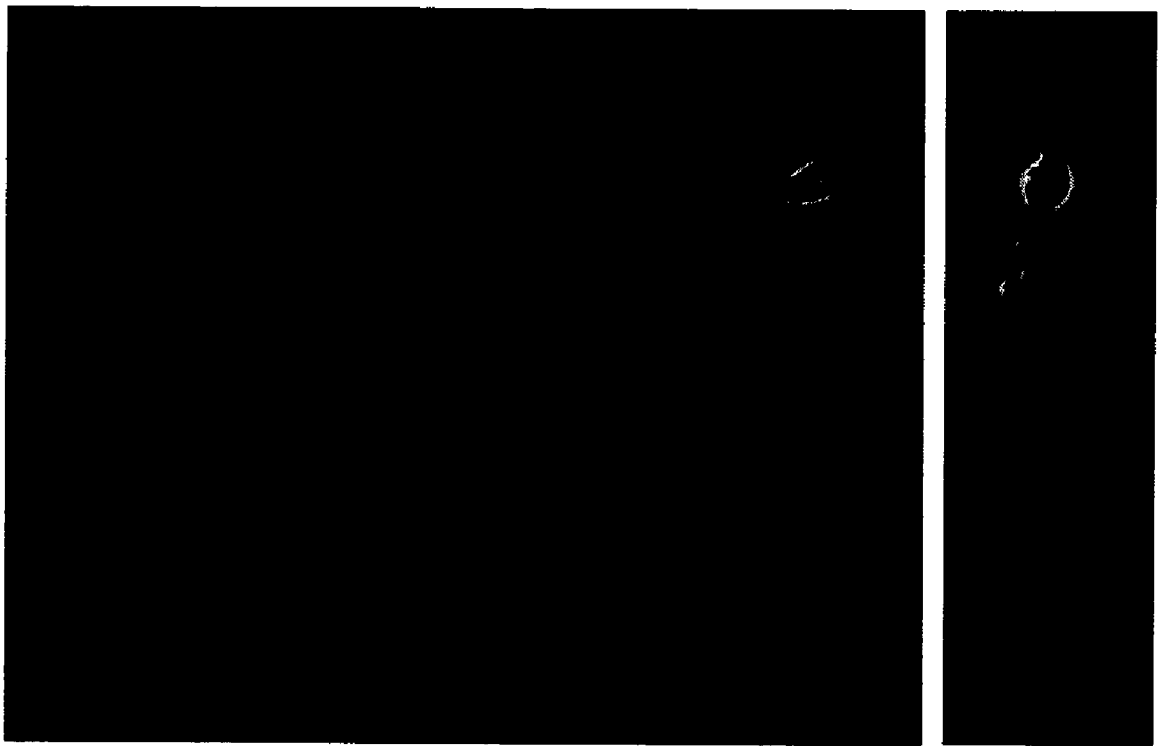
FIGS. 8A and 8B are representations of $G_{M1}$ localization in horse sperm. In 8A, two sperm are shown that represent normal patterns. The one in the upper right hand corner shows $G_{M1}$ staining predominantly in the upper half of the sperm head, while the one in the lower left corner shows staining in the lower half of the sperm head. In 8B, a sperm is shown which shows distinct $G_{M1}$ localization around an abnormality (either a proximal droplet or a "pseudo-droplet"). Interestingly, $G_{M1}$ localization in this particular sperm head also deviates from the normal patterns by appearing as a covering over the entire surface.

FIGS. 8A and 8B demonstrate that $G_{M1}$ distribution can be used as a diagnostic tool. To illustrate this embodiment, ejaculated sperm from a geriatric stallion having a defect of proximal droplets/pseudo-droplets were used. It is clear that in this figure, the morphologically-obvious defect in the proximal midpiece is accompanied by an apparent defect in localization of $G_{M1}$ in the plasma membrane of the sperm head. Therefore, this invention can reveal defects in the organization of the sperm plasma membrane which are not detectable by ordinary light microscopy.

While this invention has been described through illustrative examples, these examples are not intended to be limiting in any way and it will be recognized that routine modification can be made by those skilled in the art. Such modifications are intended to be included within the scope of the present invention.

The invention claimed is:

1. A method of determining the effect of storage media on the ability of sperm to respond to one or more stimuli associated with capacitation and/or acrosomal exocytosis, comprising the steps of:

storing the sperm in a storage media;
removing the stored sperm from the storage media;
determining a $G_{M1}$ distribution pattern in the stored sperm comprising:
  i) exposing the stored sperm to the one or more stimuli;
  ii) fixing the stored sperm in a fixative comprising paraformaldehyde, glutaraldehyde or combinations thereof;
  iii) staining the fixed stored sperm to determine the $G_{M1}$ distribution pattern in the fixed stored sperm;
obtaining a $G_{M1}$ distribution pattern of a fixed control sperm sample which has not been stored in the storage media, but which has been exposed to the same one or more stimuli, fixed in the same fixative and stained in the same manner as the fixed stored sperm; and
comparing the $G_{M1}$ distribution patterns of the fixed stored sperm and the fixed control sperm;
wherein a difference between the $G_{M1}$ distribution patters of the fixed stored sperm and fixed control sperm is indicative of an effect of the storage media on the ability of sperm to respond to one or more stimuli associated with capacitation and/or acrosomal exocytosis.

2. The method of claim 1, wherein the difference between the $G_{M1}$ distribution patterns is an abnormal localization of $G_{M1}$ within the fixed stored sperm compared to the fixed control sperm.

3. The method of claim 1, wherein the difference between the $G_{M1}$ distribution patterns is a difference in the relative frequencies of different $G_{M1}$ distribution patterns in the fixed stored sperm compared to the frequencies of the same patterns in the fixed control sperm.

4. The method of claim 1, wherein the one or more stimuli associated with capacitation is selected from the group consisting of calcium, bicarbonate, a mediator of sterol efflux and combinations thereof.

5. The method of claim 4, wherein the mediator of sterol efflux is selected from the group consisting of 2-hydroxypropyl-β-cyclodextrin, methyl-β-cyclodextrin, serum albumin, high density lipoprotein, phospholipid vesicles, liposomes and combinations thereof.

6. The method of claim 1, wherein the one or more stimuli associated with acrosomal exocytosis is selected from the group consisting of progesterone, calcium ionophore, zona pellucids proteins, lysophosphatidylcholine and combinations thereof.

7. The method of claim 1, wherein the storage medium is a cryopreservation medium.

8. The method of claim 1, wherein the storage medium is a semen extender.

9. The method of claim 1, wherein the fixative comprises 0.00400 paraformaldehyde.

10. The method of claim 1, wherein the fixative comprises 4% paraformaldehyde, 0.1% glutaraldehyde and 1 mM $CaCl_2$.

11. The method of claim 1, wherein the fixative comprises 1.25% paraformaldehyde and 2.5% glutaraldehyde.

12. The method of claim 11, wherein the fixative further comprises 100 nM sodium cacodylate and 0.5 mM $CaCl_2$.

13. The method of claim 1, wherein the sperm sample is from an individual selected from the group consisting of cat, cattle, dog, goat, guinea pig, horse, human, mouse, pig, rabbit, rat and sheep.

* * * * *

UNITED STATES PATENT AND TRADEMARK OFFICE
CERTIFICATE OF CORRECTION

PATENT NO. : 7,670,763 B2 Page 1 of 1
APPLICATION NO. : 11/591061
DATED : March 2, 2010
INVENTOR(S) : Travis et al.

It is certified that error appears in the above-identified patent and that said Letters Patent is hereby corrected as shown below:

Col. 14, line 18, Claim 1, the word "patters" should read:

--patterns--.

Signed and Sealed this

Fourteenth Day of December, 2010

David J. Kappos
*Director of the United States Patent and Trademark Office*